United States Patent [19]
Littman et al.

[11] Patent Number: 5,670,324
[45] Date of Patent: Sep. 23, 1997

[54] USE OF CHIMERIC CD4-SRC PROTEIN TYROSINE KINASES IN DRUG SCREENING AND DETECTION OF AN IMMUNE RESPONSE

[75] Inventors: Dan Littman; Hua Xu, both of San Francisco, Calif.

[73] Assignee: The Regents of the University of California, Oakland, Calif.

[21] Appl. No.: 459,964

[22] Filed: Jun. 2, 1995

Related U.S. Application Data

[62] Division of Ser. No. 112,912, Aug. 27, 1993, Pat. No. 5,439,819.

[51] Int. Cl.$^6$ .......................................... C12Q 1/68
[52] U.S. Cl. .................... 435/6; 435/15; 435/69.7
[58] Field of Search ........................ 435/6, 15, 69.7

[56] References Cited

U.S. PATENT DOCUMENTS 4,929,604  5/1990  Munford et al. .................... 514/53

OTHER PUBLICATIONS

Glover, "Recombination & Mitogenesis", *Gene cloning*, pp. 21–45 (1984).
Takeya et al., *Cell* 32, 881–890 (1983).
Littman et al., *Cell* 40, 237–346 (1985).
Marth et al., *Cell* 43, 393–404 (1985).
Quintrell et al., *Mol. Cell. Biol.* 7, 2267–2275 (1987).
Littman et al., *Nature* 325, 453–455 (1987).
Norment et al., *EMBO J.* 7, 3433–3439 (1988).
Rudd et al., *Proc. Natl. Acad. Sci. USA* 85, 5190–5194 (1988).
Veillette et al., *Cell* 55, 301–308 (1988).
Shaw et al., *Cell* 59, 627–636 (1989).
Zamoyska et al., *Nature* 342, 278–281 (1989).
Turner et al., *Cell* 60, 755–765 (1990).
Shaw et al., *Mol. Cell. Biol.* 10, 1853–1862 (1990).
Mustelin et al., *Science* 247, 1584–1587 (1990).
Cooke et al., *New Biologist* 1, 66–74 (1989).
June et al., *J. Immunol.* 144, 1591–1599 (1990).
Glaichenhaus et al., *Cell* 64, 511–520 (1991).
Klausner et al., *Cell* 64, 875–878 (1991).
Koch et al., *Science* 252, 668–674 (1991).
Molina et al., *Nature* 357, 161–164 (1992).
Straus et al., *Cell* 70, 585–593 (1992).
Waksman et al., *Nature* 358, 646–653 (1992).
Weber et al., *J. Exp. Med.* 176, 373–379 (1992).
Mayer et al., *Mol. Cell. Biol.* 12, 609–618 (1992).
Weiss, *Cell* 73.209–212 (1993).
Feig, *Science* 260, 767–768 (1993).

*Primary Examiner*—Kenneth R. Horlick
*Attorney, Agent, or Firm*—Townsend and Townsend and Crew LLP

[57] ABSTRACT

The present invention provides chimeric proteins containing extracellular and transmembrane domains of CD4 and protein tyrosine kinases of the src family. Also provided are DNA molecules encoding the proteins of the present invention and cells containing such DNA molecules. The proteins and cells of the present invention may be employed in methods for identifying drugs that block T cell activation and for identifying low level self-antigens.

10 Claims, 7 Drawing Sheets

CD4 src kinases chimeras

USE OF CHIMERIC CD4-SRC PROTEIN TYROSINE KINASES IN DRUG SCREENING AND DETECTION OF AN IMMUNE RESPONSE

This is a Division of application Ser. No. 08/112,912 filed Aug. 27, 1993, U.S. Pat. No. 5,439,819.

BACKGROUND OF THE INVENTION

The present invention relates generally to chimeric proteins comprising the extracellular and transmembrane portions of CD4 molecules and an src protein tyrosine kinases. Such CD4 chimeric proteins may amplify the signal produced by T lymphocyte stimulation. These CD4 chimeric proteins may be employed to identify drugs that block CD4+ T lymphocyte activation. The CD4 chimeric proteins are also useful for identifying self antigens that may mediate autoimmune diseases. Also provided are CD8 chimeric proteins having an src tyrosine kinase linked to the extracellular and transmembrane portions of a CD8 molecule. The CD8 chimeric proteins may be used to screen for MHC Class I restricted antigens. Both the CD4 and CD8 chimeric proteins may be employed in gene therapy treatments to enhance in vivo immunological response to specific antigens.

Cytoplasmic protein tyrosine kinases (PTK's) of the src family have important roles in signal transduction processes in multiple cell types (Bolen et al., Adv. Can. Res., 57:103–149 (1991)). Members of this family share several features: they are attached to cellular membranes through a myristylated N-terminus, they have unique N-terminal domains, and they have homologous SH3, SH2, and catalytic domains (FIG. 1A). Similar SH2 and SH3 domains are found in a wide variety of molecules involved in signal transduction (Koch et al., Science, 252:668–674 (1991)). The SH2 domains interact specifically with various proteins containing phosphotyrosine residues, whereas SH3 regions bind guanine nucleotide releasing factors, potentially linking the PTK's to the ras signaling pathway (Feig, Science, 260:767–768 (1993)). Multiple src family molecules are expressed in most cells and ablation of individual genes has resulted in developmental defects of variable severity (Soriano et al., Cell, 64:693–702 (1991); Molina et al., Nature, 357:161–164 (1992); Appleby et al., Cell, 70:751–763 (1992); stein et al., Cell, 70:741–750 (1992)). Some functions may be carried out by any one of several src family members, whereas others may only be fulfilled by a single one of these molecules.

Early activation events in T lymphocytes require the triggering of a tyrosine phosphorylation pathway that appears to involve one or more of these molecules (Weiss, Cell, 73:209–212 (1993)). A limited number of these kinases, Lck, Fyn, and Yes, are expressed in T cells. Of these, the best-characterized is the lymphocyte-specific tyrosine kinase, P56[lck] (Lck), whose unique N-terminal domain interacts with the cytoplasmic tails of the CD4 and CD8 glycoproteins. These are molecules that bind to surface MHC class II and class I molecules, respectively, and participate with the T cell antigen receptor (TCR) in early events of T cell activation (Rudd et al., Proc. Natl. Acad. Sci. USA, 85:5190–5194 (1988); Veillette et al., Cell, 55:301–308 (1988); Shaw et al., Cell, 59:627–636 (1989); Turner et al., Cell, 60:755–765 (1990); Shaw et al., Mol. Cell, Biol., 10:1853–1862 (1990)). The interaction of Lck with CD4 and CD8 is restricted to this member of the src family and is required for effective antigen-specific responses of several different T cell hybridomas (Zamoyska et al., Nature, 342:278–281 (1989); Glaichenhaus et al., Cell, 64:511–520 (1991)).

Lck apparently has multiple functions that are essential in T cell development and activation. Inactivation of the Lck gene in mice results in early arrest of thymocyte maturation, prior to cell surface expression of CD4, CD8, and the T cell receptor, suggesting that Lck has a critical function early in T cell development that is independent of these cell surface molecules (Molina et al., Nature, 357:161–164 (1992)). In the human T cell leukemic line, Jurkat, absence of Lck results in loss of activation in response to anti-TCR antibodies (Straus and Weiss, Cell, 70:585–593 (1992)). The related PTK's present in developing thymocytes and in Jurkat cells appear unable to substitute for Lck. This may be due to a requirement for Lck to associate with cell surface molecules other than CD4 and CD8 that are involved in early development and in TCR-mediated signaling.

Activation of T lymphocytes upon their encounter with MHC-bound peptide antigens is mediated through a complex machinery associated with the T cell antigen receptor (TCR). The clonally-restricted TCR provides specificity for antigen, while associated non-polymorphic polypeptides are involved in the signal transduction process (Irving and Weiss, Cell, 64:891–901 (1991); Romeo et al., Cell, 68:889–897 (1992); Letourneur and Klausner, Science, 255:79–82 (1992); Wegener et al., Cell, 68:83–95 (1992)).

In addition, the MHC-binding co-receptor molecules, CD4 and CD8, are required for initiating signals, both during thymocyte development and in the activation of mature T cells (Fung-Leung et al., Cell, 65:443–449 (1991); Rahemtulla et al., Nature, 353:180–184 (1991); Killeen et al., EMBO J., 12:1547–1553 (1993)). Apparently, signaling requires coordinate recognition of MHC by the co-receptors and by the TCR. This is achieved by binding of CD4 and CD8 to membrane-proximal domains of class II or class I molecules, respectively, while the TCR binds to the peptide-containing surface (Salter et al., Nature, 345:41–46 (1990); Aldrich et al., Nature, 352:718–721 (1991); Ingold et al., Nature, 352:721–723 (1991); Killeen et al., J. Exp. Med., 176:89–97 (1992); Glaichenhaus et al., Cell, 64:511–520 (1991); Konig et al., Nature, 356:796–798 (1992)).

The signaling cascade that follows engagement of the T cell receptor by antigen is dependent on the activity of cytoplasmic tyrosine kinases (Klausher and Samelson, Cell, 64:875–878 (1991)). Ligation of the TCR results in rapid phosphorylation of intracellular proteins on tyrosine residues (June et al., J. Immunol., 144:1591–1599 (1990)). Inhibitors of PTK function block the early signaling events, notably the phosphorylation and activation of phospholipase Cγ1, a key enzyme involved in the generation of second messengers that regulate intracellular free calcium concentration and the activity of protein kinase C (Mustelin et al., Science, 247:1584–1587 (1990)).

Several tyrosine kinases have been implicated in the initiation of the T cell signaling pathway. The lymphoid-specific cytoplasmic PTK, Lck, apparently is a key component in this process: its absence prevents TCR-mediated activation of Jurkat cells (Straus and Weiss, Cell, 70:585–593 (1992)), and PLC-γ1 has been co-precipitated with Lck following activation (Weber et al., J. Exp. Med., 176:373–379 (1992)).

A second src family PTK, Fyn-T, has also been implicated in TCR-mediated activation because it is expressed in a T cell-specific manner. Fyn-T is associated with TCR proteins in cell lysates and its level of expression correlates with the magnitude of thymocyte stimulation. A third kinase that appears to have a role in signaling is ZAP-70, a cytoplasmic PTK that is tightly associated with the TCR-ζ chain in activated T cells.

Blocking T cell function is desirable in many instances. For example, blocking T cell activation may provide a means of treating and preventing autoimmune diseases, such as systemic lupus erythematosis, rheumatoid arthritis, Sjogren's syndrome, and the like. Interfering with intracellular signal transduction following antigenic stimulation of T cells could provide a means for reducing excessive inflammation and alleviating many clinical illnesses.

Enhancement of immunological response is desirable in other clinical illnesses. For example, malignancy often impairs immune responses. In these patients, it is desirable to enhance the immune response to help fight infections as well as for primary treatment of the underlying malignancy.

No convenient means have been available to identify drugs that block T cell function at the level of protein tyrosine kinase activity. A means to identify such drugs would provide a marked advance in the art of pharmaceutical development. With such a method, skilled artisans could quickly identify promising compounds for clinical use. Quite surprisingly, the present invention fulfills these and other related needs.

SUMMARY OF THE INVENTION

The present invention provides chimeric proteins comprising a CD4 extracellular domain, a CD4 transmembrane domain, and an src family protein tyrosine kinase. These chimeric proteins may amplify the response of T cells expressing the proteins in response to immunogenic stimuli, such as antigenic stimulation and antibody cross-linking. Generally, the src protein tyrosine kinase will be a human or murine protein tyrosine kinase. Examples of such kinases include $p56^{lck}$, c-SRC, Fyn-T, or Hck, mutations of these tyrosine kinases or fusion proteins having segments of more than one tyrosine kinase. DNA molecules encoding these chimeric proteins and cells transfected with such DNA are also provided.

The CD4 chimeric proteins of the present invention may be employed to determine whether a drug is capable of blocking T lymphocyte activation. The methods generally comprise contacting the drug with a T lymphocyte that expresses a chimeric protein comprising a CD4 molecule lacking the CD4 cytoplasmic domain linked to a src protein tyrosine kinase; stimulating the T lymphocyte; observing the degree of stimulation of the T lymphocyte; and determining whether the drug is capable of blocking T lymphocyte activation therefrom.

The CD4 chimeric proteins of the present invention may also find use in methods for identifying prospective autoantigens in patients with autoimmune diseases. The methods generally comprise transfecting T lymphocytes of the patient with a DNA molecule comprising a nucleic acid sequence encoding a chimeric protein comprising a CD4 molecule lacking the CD4 cytoplasmic domain linked to an src protein tyrosine kinase; contacting the transformed T lymphocytes with antigenic material of the patient; observing stimulation of the T lymphocytes by the antigen; and determining therefrom whether the antigen elicits an immune response in the patient.

Also provided are CD8 chimeric proteins comprising a CD8 extracellular domain, a CD8 transmembrane domain, and an src protein tyrosine kinase. These CD8 chimeric proteins may be employed for identifying MMC Class I restricted antigens. The CD4 and CD8 chimeric proteins of the present invention may also be used for gene therapy to enhance the immune response.

DESCRIPTION OF SPECIFIC EMBODIMENTS

Figure 1:
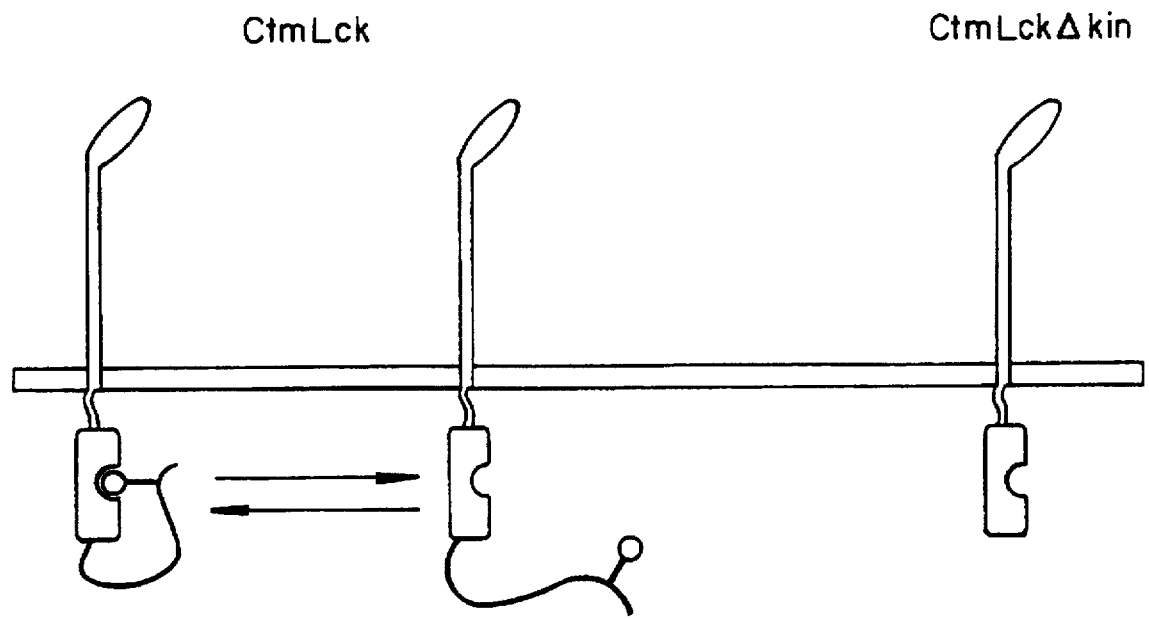
FIG. 1 is a schematic representation of removal of the kinase domain of a chimeric protein of the present invention to render SH2 more accessible.

The present invention provides chimeric proteins having a CD4 extracellular domain, a CD4 transmembrane domain, and an src protein tyrosine kinase. These CD4 chimeric proteins may amplify the response of T cells expressing the proteins in response to immunogenic stimuli, such as antigenic stimulation and antibody cross-linking. These proteins may greatly increase the sensitivity of the immune response (e.g., some CD4 chimeric proteins of the present invention may amplify T cell response by 30 times or more). By amplifying intracellular signals from immunological activation of T cells, the proteins provide a means for identifying drugs that block such intracellular signals. This provides a convenient means for screening potential drugs for the ability to block T cell activation. By blocking T cell activation, the drugs may also block harmful immune responses to antigenic stimuli, such as autoimmune diseases or graft-versus-host disease. Chimeric proteins comprising a CD8 extracellular domain, a CD8 transmembrane domain, and an src protein tyrosine kinase are also provided. These CD8 chimeric proteins may also enhance the immune response and be used to identify drugs that block CD8-mediated immune responses.

Because the chimeric proteins of the present invention may amplify the response of T cells to antigenic stimuli, low level self-antigens (as implicated in the etiology of autoimmune diseases) may be detected and identified by the present invention. DNA encoding the proteins of the present invention may be transfected into T cells of a patient suspected of suffering from an autoimmune disorder. The T cells are then exposed to tissue from the patient and observed for activation. As the T cells express chimeric proteins that amplify activating signals, even small numbers of T cells that react to the self-antigen may be detected. Both the CD4 and CD8 chimeric proteins may be used for gene therapy as described below.

The present invention provides chimeric proteins comprising a CD4 molecule lacking the CD4 cytoplasmic domain linked to an src protein tyrosine kinase. By "chimeric protein", it is meant a protein or peptide that contains subsequences that are substantially homologous to subsequences of at least two different proteins or peptides. By "substantially homologous", it is meant sequences which have at least about 65% relatedness, preferably at least 75% homology, and more preferably at least about 85–90% or more homology to the amino acid sequence of a naturally occurring CD4 molecule or protein tyrosine kinase of the src family as described in Cooper, *The src Family of Tyrosine Kinases*, in *Peptides and Protein Phosphorylation*, Kemp and Alewood eds., CRC Press, 1989. These tyrosine kinases include, e.g., p56$^{lck}$ (Lck), c-SRC, Fyn-T, Blk, Yes, Lyn, Fgr, and Hck. The tyrosine kinases may also include fusion proteins constructed from segments of different tyrosine kinases. For example, a fusion between the SH3, SH2, and kinase domains of src and the unique domain of lck is particularly effective for amplifying CD4 mediated T cell signals.

Other tyrosine kinases, such as cytoplasmic tyrosine kinases (e.g., ZAP-70), may also be employed in the chimeric proteins of the present invention. Other non-src family tyrosine kinases may be linked to the extracellular and transmembrane portions of CD4 (or CD8) molecules to form active chimeric proteins that may enhance T cell activation following immunological stimulation.

Thus, it should be understood that the polypeptide compositions of the present invention need not be identical to any particular src protein tyrosine kinase, or amino acid sequence thereof. Unless otherwise indicated, the term "src protein tyrosine kinase" or "src tyrosine kinase" will include homologs, fusions, and fragments of naturally occurring src protein tyrosine kinases as well as other tyrosine kinases, both membrane bound and cytoplasmic.

For example, naturally occurring src tyrosine kinases may be modified by introducing conservative or nonconservative substitutions in the polypeptides, usually fewer than 20 percent, more usually fewer than 10 percent of the amino acids being exchanged. It may be desirable to vary one or more particular amino acids to alter the functional characteristics of the src tyrosine kinase in T cell activation.

Therefore, the present chimeric proteins may be subject to various changes, such as insertions, deletions and substitutions, either conservative or nonconservative, where such changes might provide for certain advantages in their use. "Conservative substitutions" is intended to include, for example, combinations such as gly, ala; val, ile, leu; asp, glu; asn, gln; ser, thr; lys, arg; and phe, tyr. Usually, the sequence will not differ by more than 20% from the sequence of an src tyrosine kinase or amino acid subsequence thereof.

In addition, the amino acid sequence may differ from the natural sequence in the modification of the terminal NH$_2$ by acylation, e.g., acetylation, or thioglycolic acid amidation, terminal carboxy amidation, e.g., ammonia, methylamine, etc. In some instances, these modifications may provide increased metabolic stability, or the like, as desired.

A particularly useful src tyrosine kinase for use in the present invention is Lck. The Lck tyrosine kinase may be modified as described above for inclusion in the chimeric proteins of the present invention. The function of Lck, when bound to CD4, is not substantially affected by a point mutation that inactivates its phosphotransferase activity. Removal of the catalytic domain may give rise to a co-receptor molecule that functions better than its wild type counterpart. One of Lck kinase roles, observed in the CD4-negative T cell hybridoma transfected with activated Lck and in the Lck-negative mutant Jurkat cells apparently involves the direct or indirect association of Lck with the TCR complex through a CD4 (and CD8)-independent mechanism. In this setting, the kinase function of Lck is most likely required for signal transduction, and enhanced kinase activity may correlate with a lower threshold for activation or with constitutive activation, as exhibited by v-src-transfected hybridoma cells.

Figure 6A:
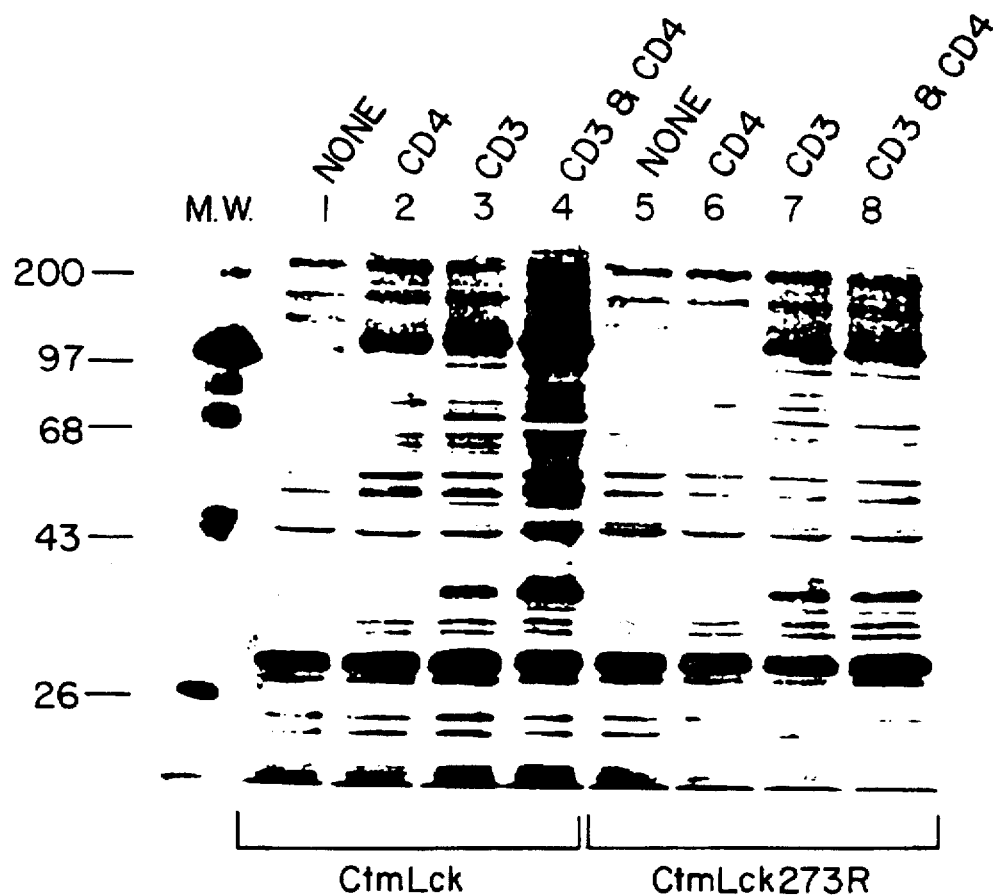
FIGS. 6A and 6B illustrate the role of CD4/Lck chimeric proteins in antibody-mediated T cell stimulation.

A point mutation ablating phosphotransferase function may impair co-receptor activity of the CD4/tyrosine kinase chimera, while truncation of the entire kinase domain may provide a molecule with enhanced activity. Generally, the truncated molecule will lack the putative regulatory tyrosine residues (e.g., tyr-394 and tyr-505 of Lck). Substitution of phe for tyr-505 activates Lck, and there is evidence that a transmembrane protein tyrosine phosphatase, CD45, regulates Lck activity by dephosphorylating this residue. In the absence of CD45, this site remains hyperphosphorylated and is thought to interact with the Lck SH2 domain, in either an inter- or intramolecular interaction. As a result, the kinase domain may be sequestered and unable to phosphorylate its appropriate substrates. The phenotypes observed with the kinase-defective chimeric molecules are consistent with this hypothesis, but, in addition, reveal an independent effector function of the SH2 domain of Lck. Reciprocal inhibition of kinase and SH2 activities due to interaction of these domains within Lck may occur in these molecules. Elimination of the kinase domain may render SH2 constitutively accessible, enhancing coreceptor activity despite the loss of phosphotransferase activity (FIG. 1). In the presence of an intact, but inactive, kinase domain decreased activity may occur, which is sensitive to a second mutation that may abolish phosphotyrosine binding by the SH2 domain. Loss of both SH2 and kinase function generally will not, however, completely eliminate coreceptor function (FIG. 6C). This kinase-independent function of CD4-associated Lck may resemble that of proteins that contain only SH2 and SH3 domains, such as Crk and sem-5/GRB2.

Figure 2A:
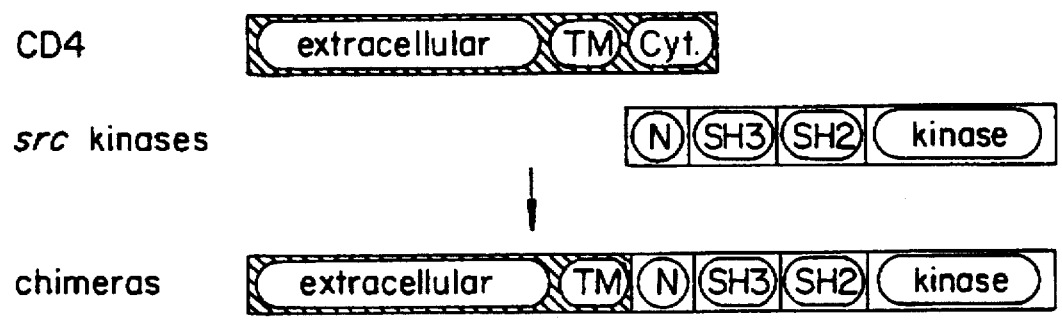
FIG. 2A illustrates the general structure of the chimeric proteins of the present invention.

In the CD4 chimeric proteins, the src tyrosine kinases are fused to the extracellular and transmembrane domains of CD4 as illustrated in FIG. 2A. Generally, the cytoplasmic domain of CD4 will not be present in the chimeric proteins. The src tyrosine kinase portion of the chimeric protein may be full length or a fragment thereof as described above. The CD8 chimeric proteins of the present invention will be similarly constructed. An src tyrosine kinase will be fused to the extracellular and transmembrane portions of a CD8 molecule.

The present invention also provide DNA molecules encoding the CD4 or CD8 chimeric proteins of the present invention. Generally, the DNA molecules of the present invention will be constructed by synthesis of a gene encoding the fusion protein in a cloning vector. For example, a plasmid encoding CD4 (such as pSM described in Turner et al., *Cell*, 60:755–765 (1990) or pMV7 as described in Glaichenhaus et al., *Cell*, 64:511–520 (1991), both of which are incorporated herein by reference) is subjected to restriction enzyme digestion to introduce a break in the CD4 coding region between the transmembrane and cytoplasmic coding domains. The resulting plasmid may then serve as a source of the CD4 extracellular and transmembrane domains for constructing the hybrids. Plasmids encoding the extracellular and transmembrane portions of CD8α or CD8β may be similarly obtained as described in Littman et al., *Cell*, 40:237–346 (1985) and Normant and Littman, *EMBO J.*, 7:3433–3439 (1988), both incorporated herein by reference.

A DNA sequence encoding an src tyrosine kinase may then be ligated to the transmembrane coding region of the above described plasmid at the restriction site. The resulting plasmid may be used to clone the fusion protein containing the extracellular and transmembrane domains of CD4 and the src tyrosine kinase.

Hybrid DNA technology will generally be employed for expression of the CD4 or CD8 chimeric proteins in transformed T lymphocytes. See, e.g., Sambrook et al., *Molecular Cloning, A Laboratory Manual*, Cold Spring Harbor Laboratory Press, 1989, incorporated herein by reference. For expression and isolation of the chimeric proteins, transfection of non-T lymphocyte host cells may be appropriate, e.g., yeast or procaryotic cells. Techniques for such recombinant production and purification of foreign proteins are well known in the art and briefly described below.

The present invention also provides DNA molecules encoding the chimeric proteins of the present invention. The DNA molecules generally comprise a transcriptional promoter, a DNA sequence encoding the chimeric protein, and a transcriptional terminator.

In general, plasmid vectors containing replication and control sequences which are compatible with the recombinant host cells are used as cloning vectors for the DNA molecules of the present invention. Other vectors, such as λ-phage, cosmids, or yeast artificial chromosomes may also be employed in some instances. The vector ordinarily carries a replication site, as well as sequences which encode proteins that are capable of providing phenotypic selection in transformed cells. For example, *E. coli* may be transformed using pBR322, a plasmid derived from an *E. coli* species. Plasmid pBR322 contains genes for ampicillin and tetracycline resistance and thus provides easy means for identifying and selecting transformed cells. The pBR322 plasmid, or microbial plasmid must also contain, or be modified to contain, promoters which can be used by the microbial organism for an expression of its own proteins. Those promoters most commonly used in recombinant DNA construction include β-lactamase (penicillinase) and lactose promoter systems and a tryptophan (trp) promoter system. One suitable promoter is contained in the in vitro transcription vector pGEM-1. The promoter is a T7 and SP6 polymerase promoter. While these are the most commonly used, other microbial promoters have been discovered and utilized, and details concerning their nucleotide sequences have been published, enabling a skilled worker to ligate them functionally with plasmid vectors. The promoters are operably linked to a nucleic acid sequence encoding the chimeric protein. The promoters may be inducible or constitutive and provide a means to express the encoded chimeric protein in the procaryotic host. Following expression, the polypeptide may be purified by standard methods such as described below.

Alternatively, a DNA sequence encoding the chimeric proteins of the present invention may be inserted into a suitable eukaryotic expression vector, which in turn is used to transfect eukaryotic cells. A eukaryotic expression vector, as used herein, is meant to indicate a DNA construct containing elements which direct the transcription and translation of DNA sequences encoding chimeric proteins of interest. Such elements include promoters, enhancers, transcription terminators and polyadenylation signals. By virtue of the inclusion of these elements operably linked within the DNA constructs, the resulting eukaryotic expression vectors contain the information necessary for expression of the polypeptides of interest.

Host cells for use in expressing recombinant chimeric proteins of interest include mammalian, avian, insect and fungal cells. Fungal cells, including species of yeast (a.g., Saccharomyces spp., Schizosaccharomyces spp.) or filamentous fungi (e.g., Aspergillus spp., Neurospora spp.) may be used as host cells for producing chimeric proteins of the present invention. Suitable vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources. The expression units may also include a transcriptional terminator. Choice of a particular host and selectable marker is well within the level of ordinary skill in the art.

Cultured mammalian cells may be used as host cells within the present invention. Cultured mammalian cells for use in the present invention may include human monocytoid, lymphocytoid, and fibroblastoid cell lines. A useful mammalian cell line is the HeLa-tat cells that are HeLa derived cells. Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041–7045, 1983); Grant et al., *Nuc. Acids Res.* 15:5496, 1987) and a mouse $V_H$ promoter (Loh et al., *Cell* 33:85–93, 1983).

Such expression vectors may also contain a set of RNA splice sites located downstream from the promoter and upstream from the DNA sequence encoding the polypeptide or protein of interest. Preferred RNA splice sites may be obtained from adenovirus and/or immunoglobulin genes. Also contained in the expression vectors is a polyadenylation signal located downstream of the coding sequence of interest.

Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the AdenoVirus 2 tripartite leader, located between the promoter and the RNA splice sites. Vectors may also include enhancer sequences, such as the SV40 enhancer and the mouse µ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973). Other techniques for introducing cloned DNA sequences into mammalian cells, such as electroporation (Neumann et al., *EMBO J.* 1:841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker such as the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

The CD4 or CD8 chimeric proteins of the present invention may be purified by a variety of means, including via affinity chromatography, e.g., on an antibody column using antibodies directed against the extracellular or transmembrane domains of CD4, antibodies directed against the extracellular or transmembrane domains of CD8, antibodies against the src tyrosine kinase, or using CD4 or CD8 binding substances, respectively. Additional purification may be achieved by conventional chemical purification means, such as liquid chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the recombinant chimeric proteins described herein; see also a purification protocol described in U.S. Pat. No. 4,929,604, incorporated herein by reference.

The CD4 chimeric proteins of the present invention may replace wild-type CD4 as a co-receptor during T cell activation. Association of CD4 extracellular and transmembrane domains with an src tyrosine kinase provides a means to mediate the function of the CD4 cytoplasmic domain in this system. The activity of the chimera required a functional CD4 extracellular domain as the chimeric protein are generally sensitive to mutations in the putative MHC class II binding site of CD4 and may be completely blocked by antibodies against CD4.

Likewise, the CD8 chimeric proteins of the present invention may replace wild-type CD8 proteins as co-receptors for activation of cytotoxic T cells. The CD8 chimeric proteins may amplify CD8 mediated T cell activation in cytotoxic lymphocytes.

Nucleic acid encoding chimeric proteins as described above may be introduced into T cells for expression. The nucleic acid may be DNA or RNA. The nucleic acid may be introduced into the T cells in by a variety of methods well known in the art and described above. Generally, the nucleic acid encoding the chimeric proteins will be introduced into the T cells by means of a retroviral vector, such as pMV7.

The retroviral vectors may be prepared as described in Glaichenhaus et al., *Cell*, 64:511–520 (1991), incorporated herein by reference. Briefly, nucleic acid encoding the chimeric proteins is introduced into a packaging cell line such as PA317 as described by Miller and Buttimore, *Mol. Cell. Biol.*, 6:2895–2902 (1986), incorporated herein by reference. Following incubation, culture supernatants are harvested and used to infect a Psi-2 cell line that provides for selection of a genetic marker carried by retroviral vectors containing nucleic acid encoding the chimeric protein. Following selection, viral stock is isolated from the infected cell line. The viral stocks may then be used to infect a T lymphocyte cell line, such as 171 cells. For screening potential drugs, it is desirable that the infected cell line be activated by a known antigen.

The infected cells may be screened to identify those cells that express the chimeric proteins. Generally, FACS analysis employing a monoclonal antibody to the CD4 region of the chimeric protein will be used to identify cells expressing the chimeric protein. Generally, analysis is facilitated if the infected T cell line does not express CD4, such as the 171.3 cell line. Alternatively, comparison of the staining pattern of infected and uninfected control T cells may be used to identify cells expressing the chimeric protein. These cells may also be sorted by FACS or magnetic beads and panning.

T cells that express the chimeric proteins of the present invention may be employed in methods for screening drugs that block T cell activation. The methods generally comprise contacting the drug with a T lymphocyte that expresses a chimeric protein comprising a CD4 molecule lacking the CD4 cytoplasmic domain linked to an src protein tyrosine kinase; stimulating the T lymphocyte; observing the degree of stimulation of the T lymphocyte; and determining whether the drug is capable of blocking T lymphocyte activation therefrom.

The T lymphocyte may be stimulated by a variety of means. For example, the T cell may be stimulated by exposure of the T cell to an antigen recognized by the T cell. Generally, exposure of the T cell to the antigen will occur in the presence of antigen-presenting cells to enhance stimulation and activation of the T cell.

Antibody cross-linking of T cell receptors (TCRs) on the cell surface may be employed to stimulate the T cells. While TCR cross-linking will initiate T cell immunological function, CD4 interaction (and associated tyrosine kinase activity) with cross-linked TCRs is required for the T cell to become fully activated. Thus, anti-TCR and anti-CD4 antibodies may be employed for T cell stimulation. Antibody cross-linking of CD4 chimeric proteins of the present invention may also be employed to activate T cells if forms of the src chimeras can activate in the absence of TCR cross-linking (e.g., carboxy-terminal mutations of src kinases, such as a Phe to Tyr substitution at amino acid position 505 in Lck or position 527 in SRC).

The degree of stimulation of the T cells is then observed. Among the many ways the degree of T cell stimulation may be quantified, measuring observable products of T cell activation is often the most convenient. Such products include interleukin-2 synthesis. Supernatant from stimulated T cells may be titrated in dilutions with cytotoxic T lymphocytes. Proliferation of cytotoxic T lymphocytes may then be induced by treatment with a mitogen such as 3-(4,5-dimethylthiazol-2-yl)-2,5 diphenyltetrazolium bromide. Drugs blocking T cell activation will generally decrease the synthesis of interleukin-2 by stimulated T cells.

Alternatively, rapid colorimetric assays for interleukin-2 promoter driven reporter molecules may be employed. Such reporter molecules include, e.g., secreted alkaline phosphatase and β-galactosidase. Assays for such reporter molecules are well known in the art and may provide an indirect means for identifying activation of the interleukin-2 promoter, and hence indicate increased interleukin-2 production.

Alternative means of measuring the degree of T cell stimulation include, e.g., determining the degree of activity of the src protein tyrosine kinases in stimulated T cells. As the tyrosine kinases will phosphorylate tyrosine residues following T cell activation, quantification of such phosphorylation may be used to assess the degree of blocking of T cell activation by a drug. Intracellular protein phosphorylation may be determined by immunoblotting with monoclonal antibodies specific for phosphorylated tyrosine residues.

The chimeric proteins of the present invention may also be employed in methods for detection of low level self-antigens suspected of causing autoimmune disease. The methods generally comprise transfecting T lymphocytes of the patient with a DNA molecule comprising a nucleic acid sequence encoding a chimeric protein comprising a CD4 molecule lacking the CD4 cytoplasmic domain linked to an src protein tyrosine kinase; contacting the transformed T lymphocytes with the patient's antigen; observing stimulation of the T lymphocytes by the antigen; and determining therefrom whether the antigen elicits an immune response in the patient. Cells expressing CD8 chimeric proteins may be employed in similar methods for identifying low-level MHC Class I restricted antigens.

The patient's T cells may be transfected with DNA encoding a chimeric protein of the present invention by a variety of means well known to those of skill in the art. Generally, a retroviral vector as described above will be employed to transfect the patient's T cells. Alternatively, other methods for transfecting eukaryotic cells, such as calcium phosphate-mediated transfection or electroporation. Typically, chimeric proteins having more activity than naturally occurring src protein kinases will be employed in these screening methods. Cells expressing the chimeric proteins of the present invention may be identified by FACS as described above.

Following identification of cells expressing the chimeric proteins of the present invention, the cells are contacted with the suspected antigen. To demonstrate that patient T cells react with a self-antigen, a crude extract from patient tissue may be employed to stimulate the T cells. As the transfected patient T cells will generally exhibit a greater degree of activation to antigenic stimulation, even self-antigens present in low levels may be detected by observing the transfected T cells. Observation of T cell activation, e.g., by increased interleukin-2 synthesis or increased protein tyrosine phosphorylation, may indicate that T cells of the patient may be activated by a self-antigen.

Self-antigens may also be identified by similar methods. Fractions of crude patient tissue extracts may be tested against patient T cells transfected with DNA encoding chimeric proteins of the present invention. Identification of T cell activation in a fraction indicates that a self-antigen is present in that fraction. The active fraction may then be fractionated and the resulting samples similarly tested against the patient's transfected T cells. This process may be repeated until the antigen is purified. The purified antigen may then be identified by methods well known to those of skill in the art.

DNA molecules encoding the chimeric proteins of the present invention may be employed for gene therapy for enhancing a desired immune response. Antigen-specific T cells could be isolated from a patient and transfected with DNA of the present invention. Expression of the encoded chimeric proteins could be determined and the cells reinfused into the patient. The transformed cells expressing the chimeric proteins may demonstrate an enhanced immune response to the chosen antigen, thereby enhancing immunological removal of the antigen.

One particularly useful application of gene therapy employing the DNA molecules of the present invention is enhancement of cytotoxic T cell activity against tumors. Cytotoxic T cells specific for the tumor may be isolated from tumor tissue. The T cells may be transfected with a DNA molecule encoding a CD8 chimeric protein, such as a CD8-Lck chimera. The cells may be re-infused into the patient and exhibit enhanced tumor killing ability. Such treatment is especially attractive as T cells from animals with malignancies have been shown to have a reduced level of tyrosine kinases.

The following examples are offered by way of illustration and not limitation.

EXAMPLES

The following enzymes and antibodies were used in the following examples. The Pfu polymerase was purchased from Strategene. MAbs GK1.5 (anti-murine CD4), 2C11-145 (anti-murine, CD3), 519 (anti-mouse $\beta$2-microglobulin), and 4G10 (anti-phosphotyrosine) were used as hybridoma culture supernatants. The phycoerythrin-conjugated GK1.5 was purchased from Becton Dickinson. Peroxidase-labeled goat anti-rabbit IgG was purchased from Kirkegaard & Perry Laboratories. Goat anti-mouse IgG-POD conjugate was from Boehringer Mannheim.

Cell lines used in the following examples were as follows. The T cell hybridoma 171 has been previously described (Glaichenhaus et al., Cell, 64:511–520 (1991), incorporated herein by reference). The cell line produces monoclonal antibodies specific for a hen egg lysozyme peptide corresponding to residues 74–88 (NLANIPASALLSSDI) in association with the I-A$^b$ MHC molecule. A subclone of this cell line, 171.3, was used in all experiments. The FT7.1 cell line is a derivative of L cells that express both the $\alpha$ and $\beta$ chains of the A$^b$ MHC class II molecule (Ronchese et al., J. Immunol., 139:629–638 (1987), incorporated herein by reference). All cells were grown in Dulbecco's modified Eagle's medium supplemented with 10% fetal bovine serum (FCS), 50 $\mu$M 2-mercaptoethanol, 100 Unit/ml penicillin G, and 100 $\mu$g/ml streptomycin. For the IL-2 indicator cell line CTLL, the medium also contained 10 mM Hepes, pH7.4, vitamins and nonessential amino acids in addition to 60 unit/ml recombinant human IL-2 (purchased from Amgen or R&D; the activity of the R&D product was normalized to that of the Amgen product).

Transient transfection of COS7 cells with CD4-based constructs and immunoprecipitation analyses and kinase assays of the chimeric proteins were performed as previously described (Turner et al., Cell, 60:755–765 (1990), incorporated herein by reference. T cells were analyzed by the following procedure: $10^7$ cells were pelleted and washed once with cold PBS. The cells were lysed in 1 ml lysis buffer (137 mM NaCl, 1 mM EDTA, 10% glycerol, 0.5% Triton X-100, and 50 mM Tris-HCl, pH 8.0) in the presence of protease inhibitors (10 $\mu$g/ml leupeptin, 10 $\mu$g/ml soy bean trypsin inhibitor, 2 $\mu$g/ml pepstatin, 500 unit/ml aprotinin, and 1 mM PMSF) and the tyrosine phosphatase inhibitor sodium orthovanadate at 2.5 mM. The lysate was cleared by a 5 minute centrifugation at 4° C. and then incubated with 40 $\mu$l of goat anti-rat IgG-Sepharose beads (Sigma) pro-armed with the anti-CD4 MAb GK1.5. Immunoprecipitation was allowed to continue for 2 hours at 4° C. The beads were washed 3 times with cold PBS, 5 mM EDTA, 0.5% NP-40. The beads were then resuspended in 1 ml kinase buffer (10 mM MnCl$_2$ and 50 mM Tris-HCl, pH7.5) and divided into 30% for the kinase assay and 70% for immunoblotting. For the kinase assay, the beads were incubated in 15 $\mu$l kinase buffer containing 20 $\mu$Ci $\gamma$-$^{32}$P-ATP (3000Ci/mM, Amersham) and 10 $\mu$g acid-denatured enolase (Sigma). After 5 minutes at room temperature, 15 $\mu$l of 2× nonreducing SDS sample buffer was added to stop the reaction. The reaction product was analyzed by SDS-PAGE. The gel was fixed, treated with 1 M KOH at 55° C. for 1 hour to remove serine/threonine phosphorylation, and refixed before being dried down for autoradiography. For immunoblotting, the beads were denatured in nonreducing sample buffer. Half of each sample was electrophoresed on SDS-PAGE and transferred to a nitrocellulose membrane. The filter was blocked in 5% dried milk in TBST (10 mM Tris.Cl, pH8, 0.9% NaCl, and 0.1% Tween-200, incubated in appropriately diluted rabbit antiserum against murine CD4 or Lck, followed by peroxidase-labeled anti-rabbit IgG (1:10,000 dilution), and then developed using the ECL detection system (Amersham).

Antibody-mediated crosslinking was performed as follows: $10^7$ T cells were centrifuged and washed once with cold media without FCS. The washed cells were incubated on ice with 0.5 ml of the appropriate MAb(s) at saturating concentration for 30 minutes. Fourteen mls of cold PBS was added to the tube and the cells were collected by centrifugation. The cells were resuspended in 100 µl media without FCS and transferred to an eppendorf tube. After 3 minutes at 37° C., 2 µg of rabbit, anti-hamster IgG was added to the cells. The tube was immediately returned to 37° C. and the incubation continued (usually for 2 minutes, except for the time course experiments). The cells were lysed on ice by mixing quickly with 100 µl of ice-cold 2× lysis buffer which contained 2% NP-40 (instead of Triton X-100) and inhibitors of proteases and phosphatases. The lysate was cleared by centrifugation. For blotting of total cellular proteins, the lysate was denatured by the addition of 100 µl 2× nonreducing SDS sample buffer. For immunoprecipitation of Lck 800 µl of cold lysis buffer without detergent was added, and the lysate was incubated with MAb A4 (anti-human Lck)-armed anti-mouse agarose beads for two hours at 4° C. The beads were washed 3 times with TBST+10 mM EDTA+1 mM sodium orthovanadate before addition of 40 µL of 2× nonreducing sample buffer. Denatured samples were resolved by SDS-PAGE and transferred to a nitrocellulose membrane. Proteins phosphorylated on tyrosine residues were detected by immunoblotting using MAb 4G10 as the primary antibody followed by peroxidase coupled goat anti-mouse IgG at 1:20,000 dilution. The blot was developed by the ECL method.

Example 1

Construction of Plasmids Encoding the Chimeric Proteins

This example demonstrates construction of plasmids encoding chimeric proteins of the present invention. Several of the chimeric proteins contained subsequences having mutations of the corresponding wild-type protein. The plasmids produced in this example provided a source of chimeric proteins for use in assays.

A Xba I site was introduced into the mouse CD4 cDNA in the pSM vector (Turner et al., *Cell*, 60:755–765 (1990), incorporated herein by reference) at residue 394 (the end of the transmembrane domain) by oligonucleotide-directed mutagenesis, resulting in a serine substitution for cys-395 (the numbering of the residues is according to Littman and Gettner, *Nature*, 352:453–455 (1987)). The resulting plasmid was used as the source of the CD4 extracellular and transmembrane domains for constructing the hybrids. A Xho I site was introduced into tho murine lck cDNA in pSM at the sequence corresponding to amino acid residue 5. (Marth et al., *Cell*, 43:393–404 (1985).

The CD4 and Lck sequences were ligated together in the presence of a pair of annealed complementary oligonucleotides bridging the 3' CD4 Xba I and the 5' lck Xho I sites, giving rise to CtmLck containing the CD4 cDNA up to residue 396 and the whole Lck sequence (residues 1-509 with the first amino acid replaced by lysine). To construct other chimeras, the entire coding sequences of chicken c-src (Takeya and Hanafusa, *Cell*, 32:881–890 (1983), mouse fyn-T (Cooke and Perlmutter, *New Biologist*, 1:66–74 (1990) and human hck (Quintrell et al., *Mol . Cell. Biol.*, 7:2267–2275 (1987) were amplified by the polymerase chain reaction using the Pfu polymerase, which has a low mutation frequency, under conditions suggested by the manufacturer. The 5' primer contained a Xba I site to facilitate the ligation of the PCR products with the CD4 cDNA missing the cytoplasmic domain. The junctions between CD4 and src family kinases were sequenced.

FIG. 2A is a schematic representation of the chimeras between CD4 and src-family PTK's. The extracellular, transmembrane, and cytoplasmic domains of CD4 and the unique N-terminal, SH3, SH2, and kinase domains of the PTK's are indicated. The drawing is not to scale. The chimeras are designated by Ctm followed by the name of the particular kinase. For example, CtmLck indicates the hybrid of CD4 and Lck.

Chimeras containing various mutations were generated by a 2-step process: the mutations were first introduced into lck by oligonucleotide-directed mutagenesis; then part of the lck cDNA containing the mutation was swapped into the chimera using standard methods. In the CtmLck273R mutant, lys-273 of Lck, which is essential for kinase activity, was substituted with arginine; in the CtmLck154K mutant, arg-154 of Lck, which is predicted to be critical for phosphotyrosine-binding, was replaced with lysine; the CtmLck273R154K mutant was obtained by combining both of the above mutations; in the kinase domain truncation mutant, residues 249-505 of lck were deleted using a bridging oligonucleotide. Mutations at the putative CD4 MHC class II binding site (the MM4 mutants) were generated by changing residues 101-107 (Lys-Val-Thr-Phe-Ser-Pro-Gly) to Gly-Leu-Thr-Thr-Thr-Thr-Thr. All the mutations were verified by sequencing.

The chimeras were initially made in the pSM vector for analysis in COS7 cells. They were subsequently cloned into the pMV7 vector for preparation of retroviral packaging cell lines (Glaichenhaus et al., supra).

Example 2

Preparation of Retroviral Packaging Cell Lines and Isolation of Infected T Cells This example demonstrates preparation of packaging cells producing retroviral vectors containing chimeric proteins of the present invention. Following preparation of the packaging cells, T lymphocytes were infected with retroviral vectors encoding chimeric proteins.

The preparation of the packaging cells producing retrovirus encoding the various CD4-containing proteins and the subsequent infection of 171.3 cells were as described by Glaichenhaus et al., supra. Cells expressing CD4 on their surface were either selected by FACS (Glaichenhaus et al., supra) or sorted using magnetic beads, as outlined below. Two days after infection, $10^7$ T cells were incubated with the anti-CD4 MAb GK1.5 at saturating concentration for 30 minutes on ice. The cells were washed extensively with phosphate-buffered saline (PBS) plus 2% FCS. The cells were mixed with $4\times10^8$ Dynabeads M-450 coated with sheep anti-rat IgG (Bioproducts for Sciences, Inc.), pelleted, and allowed to stand on ice for 30 minutes. The cell/bead mixture was resuspended in 100 µl PBS plus 2% FCS and the incubation was continued for another 30 minutes. Cells bound to beads were separated from the unbound cells by magnetic force. The beads and cells were resuspended in 5 ml PBS plus 2% FCS and then isolated again using the magnet. This process was repeated an additional 3 times. After three days in culture, bead-purified cells that had detached from the beads were separated and discarded, and the culture was continued for three more days. The remaining cells that had detached from the beads were expanded. To obtain cells expressing similar levels of surface CD4, the above sorted cell lines were resorted by FACS, using a narrow window of fluorescence intensity.

Example 3

Analysis of Cell Surface CD4 Expression

This example demonstrates detection of cell surface expression of CD4 antigens on transfected cells.

Approximately $5 \times 10^5$ cells (either transfected COS7 cells or sorted T cells) were stained with 100 µl phycoerythrin-conjugated GK1.5 at saturating concentration (1:200 dilution) and then resuspended in PBS, 2% FCS, and 0.2 µg/ml propidium iodide. Cell surface fluorescence was analyzed on a FACScan (Becton-Dickinson), and the dead cells were gated out by their high propidium iodide staining.

The 171.3-derived cells were stained with phycoerythrin-conjugated anti-CD4 MAb GK1-5 and analyzed by flow cytometry. The parental 171.3 cells do not express CD4 and represent the negative staining profile (unfilled line in each panel). Each cell population was obtained by cell sorting following infection with retrovirus encoding the following: wild type CD4 (CD4); CD4 with a cysteine to alanine substitution in the cytoplasmic domain (CD4MCA1); CD4 mutated in the MHC class II binding site (CD4MM4); CD4/lck chimera (CtmLck); CD4/lck chimeras containing mutations in the class II binding site (CtmLckMM4), the catalytic domain (CtmLck273R), the SH2 domain (CtmLck154K), and both the kinase and SH2 domains (CtmLck273R154K); CD4/lck chimera lacking the kinase domain (CtmLckΔkin); CD4 chimeras containing Src, Fyn T, and Hck (CtmSrc,CtmFynT, and CtmHck).

Figure 2B:
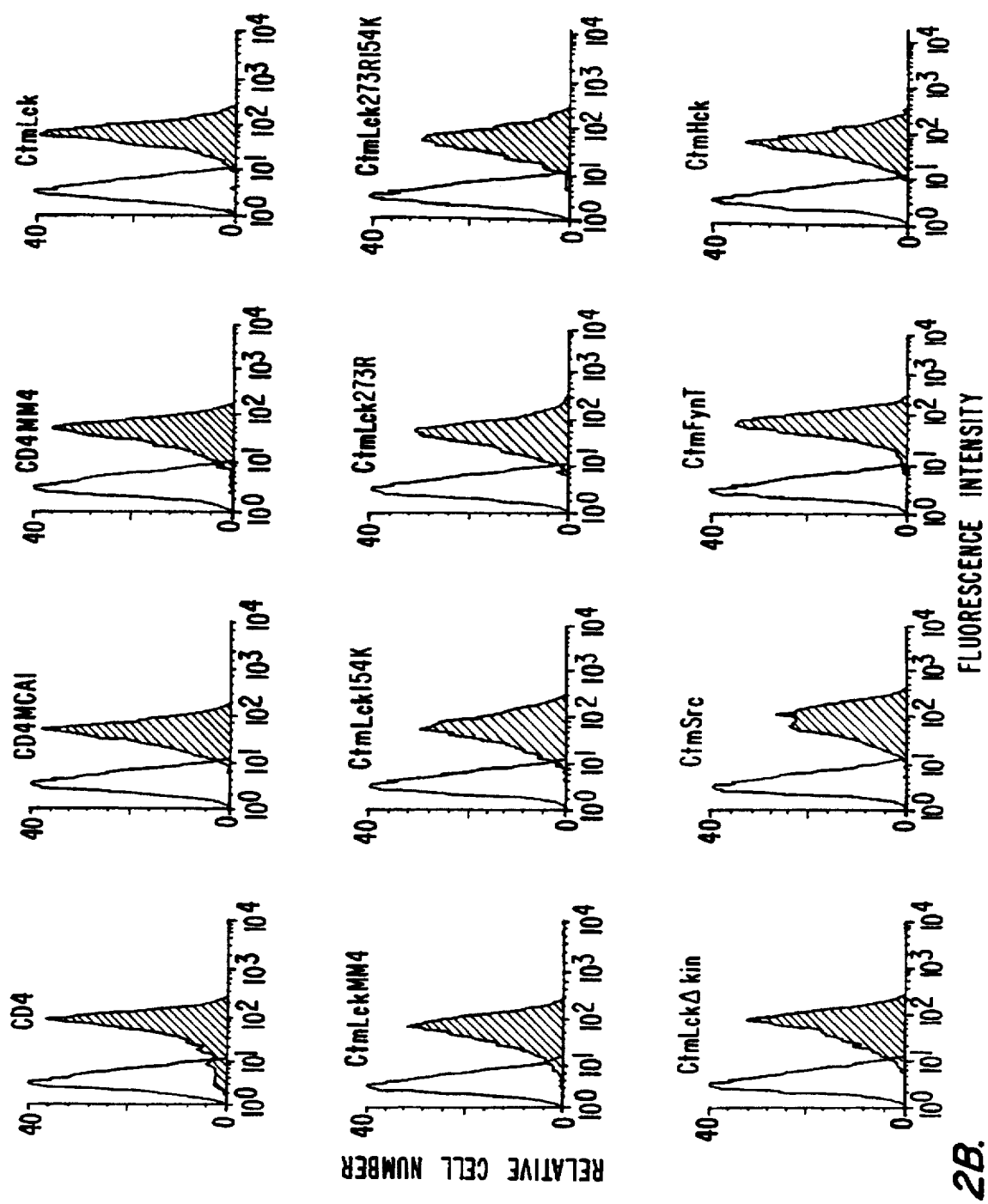
FIG. 2B illustrates T cell surface expression of CD4 and the chimeric proteins of the present invention.

The different sorted cell lines expressed roughly equivalent levels of both surface CD4 (FIG. 2B) and TCR/CD3. FACS analyses showed that all of the chimeric molecules were expressed at similar levels on the cell surface (FIG. 2B).

Example 4

Function of CD4/Lck Chimeric Protein During T cell Activation

This example demonstrates that CD4/LCK chimeric molecules may function as a co-receptor during T cell activation. T cells expressing the CD4/Lck chimeric protein were readily activated upon stimulation with the T cell-specific antigen.

A DNA sequence encoding a chimeric protein consisting of the extracellular and transmembrane domains of CD4 linked to the entire Lck protein was constructed as described in Example 1. The CD4 cytoplasmic domain was omitted from this hybrid protein to avoid CD4 interaction with endogenous T cell Lck. The cDNA was first cloned into an SV40-based vector (pSM) and shown to direct expression of surface CD4 upon transient transfection into COS7 cells. The fusion protein was immunoprecipitated from lysates of these cells with anti-CD4 antibody and demonstrated to have in vitro kinase activity. The construct was then introduced via retrovirus-mediated gene transfer into the antigen-specific T cell hybridoma line 171.3 that requires CD4 expression for activation (Glaichenhaus et al., supra).

Activation of the 171 cells and measurement of IL-2 production were as described by Glaichenhaus et al., supra, previously incorporated herein by reference. For the antibody blocking experiments, 25 µl of the anti-CD4 or anti-β2microglobulin hybridoma supernatants was also added to the mixture of T cells, antigen, and antigen presenting cells.

Figure 3A:
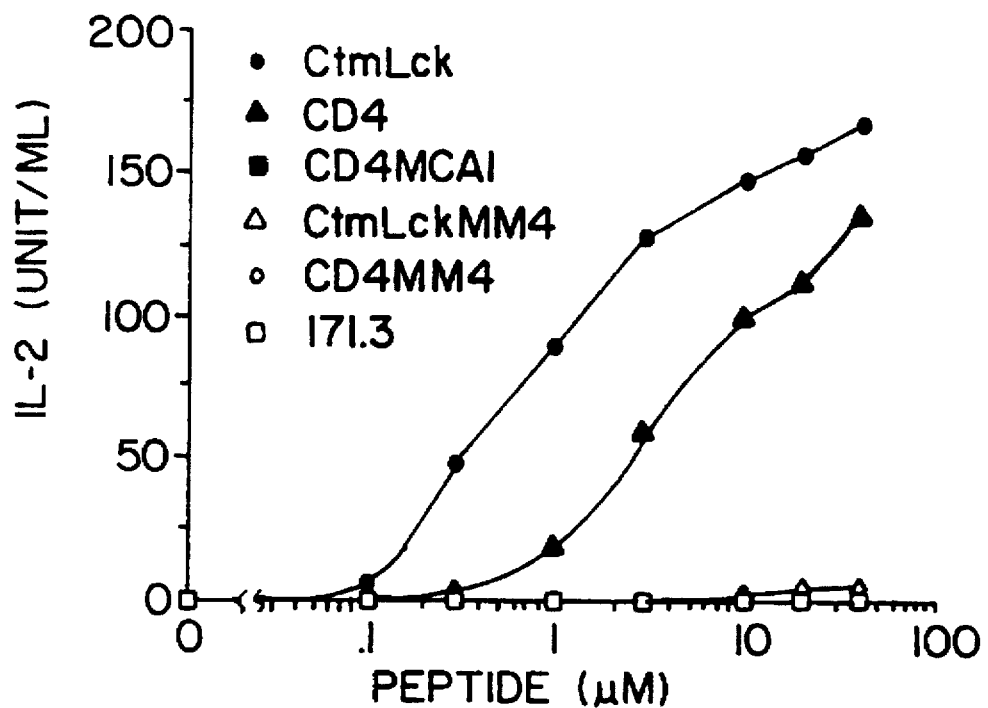
FIGS. 3A and 3B illustrate the antigen-specific response of T cells expressing the CtmLck chimeric protein.

Infected cells were sorted to establish a polyclonal cell line expressing the chimeric protein. The same approach was used to prepare cell lines expressing the other constructs described below. The CD4+ cell lines were then tested for their response to stimulation with the antigen, a synthetic peptide analog of hen egg lysozyme, in the presence of antigen-presenting cells expressing the appropriate class II molecule, I-A$^b$. FIG. 3A illustrates a comparison of responses of T cells expressing no CD4 (the parental 171.3 cells), the CD4/lck chimeric molecule (CtmLck), wild type CD4, mutant CD4 (MCA1) that does not bind p56$^{lck}$, and mutant CD4 (MM4) or CD4/lck chimera (CtmLckMM4) that do not bind MHC class II. The T cells were stimulated by co-culturing with the appropriate antigen presenting cells and the peptide antigen at indicated concentrations.

In contrast to the parental CD4-negative 171.3 cells, these cells (CtmLck) were readily activated upon antigen stimulation, as were cells that expressed wild type CD4 (FIG. 3A). As was previously demonstrated, a form of CD4 with a mutation in one of the cysteine residues required for binding of endogenous Lck (CD4MCA1) mediated a barely-detectable response to antigen. Thus, the chimeric molecule functionally resembles wild-type CD4, to which Lck is bound non-covalently.

Figure 3B:
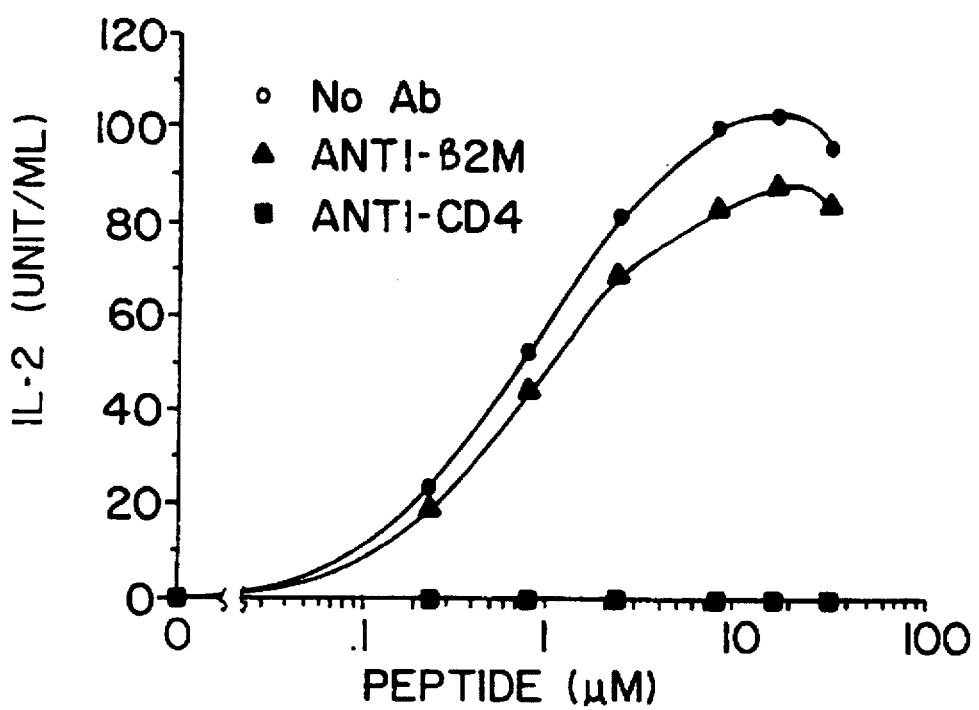

Activated forms of src family kinases can increase IL-2 responses in the absence of a co-receptor interaction with ligand. For example, overexpression of an activated form of Lck has been previously shown to enhance responsiveness of a CD4- T cell hybridoma to stimulation with antigen (Abraham et al., Nature, 350:62–66 (1991). In addition, expression of viral src in another T cell line resulted in constitutive IL-2 expression (O'Shea et al., 1991). In order to rule out the possibility that the mode of action of the CD4/lck chimera was through constitutive activity of the PTK that lowered the threshold for activation, the reported MHC class II binding site of CD4 (Lamarre et al., Science, 245:743–746 (1989); Clayton et al., Nature, 339:548–551 (1989), both of which are incorporated herein by reference) was mutated and assayed for functional activity. This mutation completely abolished the function of both CD4 and the CD4/lck chimera (CD4MM4 and CtmLckMM4 in FIG. 3A). The defect in these molecules was confined to the function of the extracellular domain, since antibody-mediated crosslinking of CD3 and the mutant CD4 or CD4/lck chimera resulted in normal levels of tyrosine phosphorylation of cellular substrates and the in vitro kinase activity of the MHC-non-binding mutant chimeric molecule was similar to that of the CtmLck molecule. In addition, the activity of the chimeric molecule in the T cell hybridoma was completely blocked by antibody against CD4 but not by a control MAb against β$_2$-microglobulin used as a control (FIG. 3B). These results indicate that, like wild type CD4, a functional class II-binding extracellular domain is essential for the activity of the CD4/lck hybrid molecule and confirms that this molecule is appropriately regulated in the 171.3 hybridoma.

Example 5

Function of CD4 Chimeric Proteins Having a non-Lck Tyrosine Kinase

This example describes functional assays of CD4 chimeric proteins having non-Lck src tyrosine kinases. The chimeric proteins displayed co-receptor function in response to antigen.

Figure 4A:
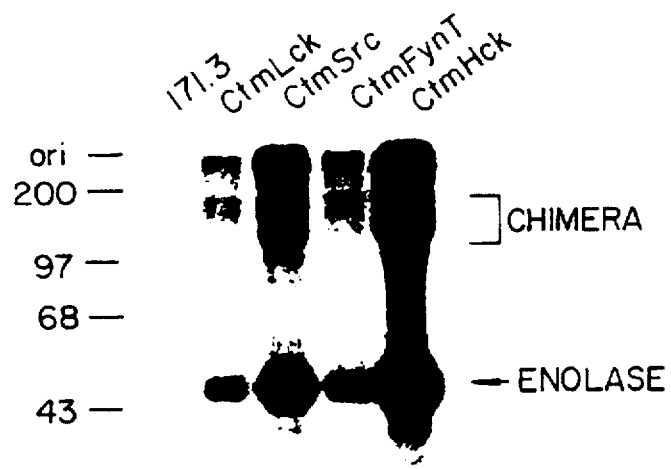
FIGS. 4A and 4B illustrate analysis of T cells expressing chimeric proteins of the present invention that contain non-Lck src family tyrosine kinases.

Polyclonal populations of cells derived from the 171.3 hybridoma expressing the various chimeric proteins were prepared and tested for their response to antigen. The expression of the T cell receptor complex was nearly identical in all cells with the exception of those expressing CtmHck, whose TCR/CD3 level was approximately 60% that of the other lines. Chimeric proteins were precipitated from the sorted cell lines using anti-CD4 antibodies. Acid-denatured enolase was included in the kinase reactions to serve as a model substrate. The reaction was analyzed on 10% SDS-PAGE. The chimeric proteins were shown to have kinase activity (FIG. 4A).

Figure 4B:
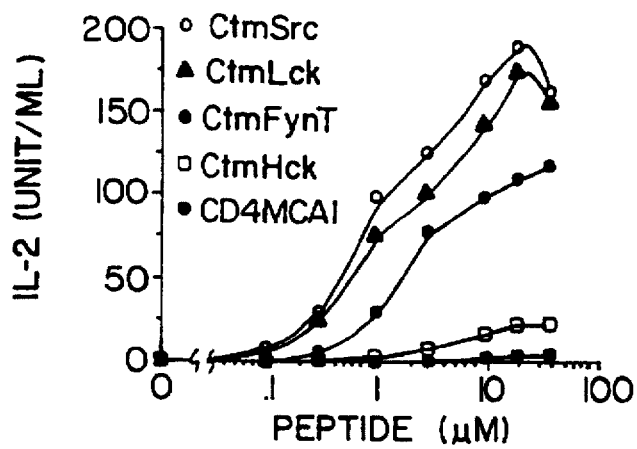

All chimeric proteins displayed co-receptor function in response to antigen when co-cultured with antigen-presenting cells and peptide antigen (FIG. 4B), although cells expressing the CD4/hck hybrid protein were considerably less responsive than cells expressing the other molecules. The results indicate that, when appropriately localized within the cell, e.g. tethered to CD4, different members of the src family may be functionally interchangeable.

Example 6

An Active Kinase Domain is not Essential for the Function of the CD4/lck Chimera This example demonstrates that the tyrosine kinase domain of the chimeric proteins need not be active to provide a functional chimeric protein.

Protein phosphorylation on tyrosine residues has been shown to play an essential role in TCR-mediated activation of T cells (June et al., *Proc. Natl. Acad. Sci. USA*, 87:7722–7726 (1990). In addition, crosslinking of CD4 to the TCR/CD3 complex results in a significant enhancement in cytoplasmic PTK activity and in signal transduction (June et al., supra). Two forms of the CD4/lck chimera that were defective in phosphotransferase activity and expressed these in the T cell hybridoma were prepared. The chimeras were immunoprecipitated using an anti-CD4 MAb from T cell lysates; kinase reactions were initiated by addition of $\gamma$-$^{32}$P-ATP. Acid-denatured enolase was used as a model kinase substrate. The reaction products were separated by SDS-PAGE and visualized by autoradiography.

Figure 5A:
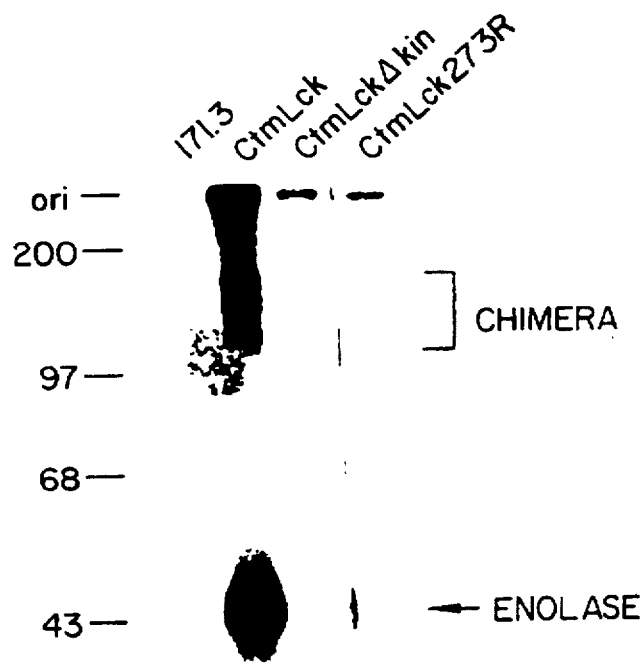
FIGS. 5A–5C illustrate the effect of ablation of the kinase activity on the function of CtmLck chimeric proteins.
Figure 5B:
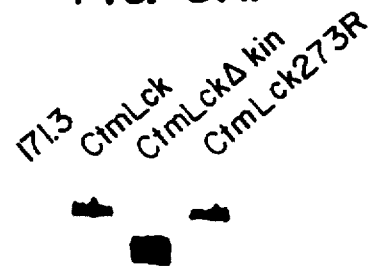
Figure 5C:
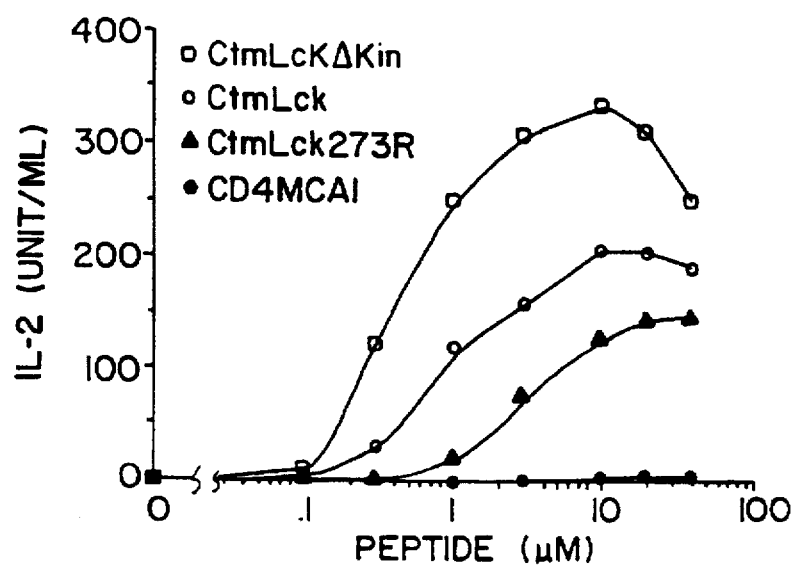

Both a point mutation in a residue essential for phosphotransferase activity (CtmLck273R, lys-273 of Lck converted arg) or a truncation of the entire, kinase domain (CtmLckΔkin, missing residues 249–505 of Lck) resulted in complete loss of the in vitro kinase activity of the chimeric proteins. (FIGS. 5A & 5B). The mutant CD4/lck lacking the entire catalytic domain rendered the hybridoma highly responsive to antigen stimulation when co-cultured with peptide antigen at various concentrations in the presence of antigen-presenting cells (FIG. 5C). The chimera with a substitution for lys-273 also showed substantial, though reduced, co-receptor activity. A CD4/hck chimeric molecule with an analogous point mutation also retained biological activity that was similar to that of its wild-type counterpart. These results indicate that, in antigen-specific T cell activation, the function of CD4-associated Lck does not exclusively rely on its enzymatic activity and that non-catalytic properties of src family PTK's can contribute directly to at least some of their functions.

Previous studies have shown that antibody crosslinking of the TCR-complex leads to the activation of a protein tyrosine kinase pathway, and that co-crosslinking of CD4 with the TCR significantly enhances this process (June et al., *J. Immunol.*, 144:1591–1599 (1990)). To determine whether this enhancement is dependent on the catalytic activity of CD4-associated Lck, the effects of the wild type and the kinase-defective CD4/lck proteins on TCR-induced protein tyrosine phosphorylation were analyzed using antiphosphotyrosine immunoblots. Crosslinking was performed with the indicated MAbs against murine CD4 or/and CD3 plus secondary antibodies at 37° C. for 2 minutes. Phosphotyrosine-containing proteins were detected by immunoblotting. Lysate from 1.5×10$^6$ cells was applied to each lane. T cells expressing the CD4/lck chimera are in lanes 1–4 and its kinase-negative mutant lanes 5–8 in FIG. 6A. Aggregation of the CD4/lck chimera (approximately 108 kd) with anti-CD4 antibody resulted in its own tyrosine phosphorylation (lane 2). Treatment with anti-CD3 antibody resulted in the specific tyrosine phosphorylation of several proteins, with prominent bands observed at 36 kd, 72 kd, and 110 kd. Coaggregation of the chimera with the TCR/CD3 complex significantly enhanced the tyrosine phosphorylation of these cellular proteins (lanes 3 and 4). In contrast, crosslinking of the kinase-defective mutant chimera did not result in its phosphorylation (lane 6), nor was protein tyrosine phosphorylation significantly augmented by its co-crosslinking with the TCR/CD3 complex (lanes 7 and 8). Similar results were also obtained in a time course study.

Figure 6B:
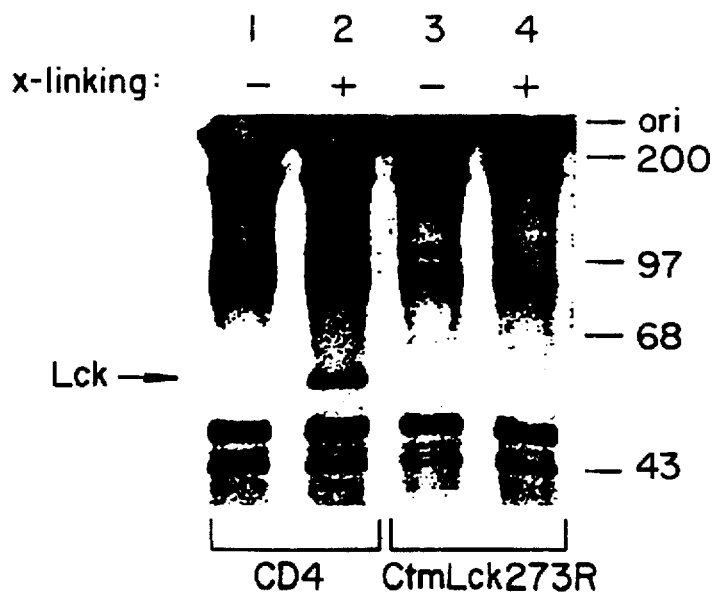

These data indicate that it is unlikely that the kinase-defective mutant chimeric proteins function in the antigen-specific response due to their association with an endogenous kinase (including Lck). This conclusion is reinforced by the inability to co-immunoprecipitate endogenous Lck or another kinase activity with the chimera under a variety of different conditions. To further examine the possibility of a functional association between endogenous Lck and the chimeric protein, the tyrosine-phosphorylation status of Lck following antibody-mediated crosslinking of the kinase-negative chimera was analyzed (FIG. 6B). Crosslinking was carried out for 2 minutes at 37° C. Lck was then immunoprecipitated from the cell lysates and analyzed by anti-phosphotyrosine immunoblot. Cells expressing wild type CD4 were used as a positive control (lanes 1-2).

Immunoprecipitated Lck from lysates of untreated or anti-CD4 treated cells was analyzed by immunoblotting with an anti-phosphotyrosine MAb. Crosslinking of wild type CD4 resulted in the heavy phosphorylation of Lck on tyrosine, but no such change was detectable, in cells expressing the kinase-deficient chimeric protein. Reprobing of the same niter with anti-Lck antibodies following stripping revealed similar levels of Lck in all immunoprecipitates.

Example 7

The SH2 Domain of Lck Mediates the Co-Receptor Activity of the CD4/lck Chimera

This example demonstrates that the SH2 domain of Lck is involved in mediating co-receptor activity of the chimeric proteins.

Figure 7C:
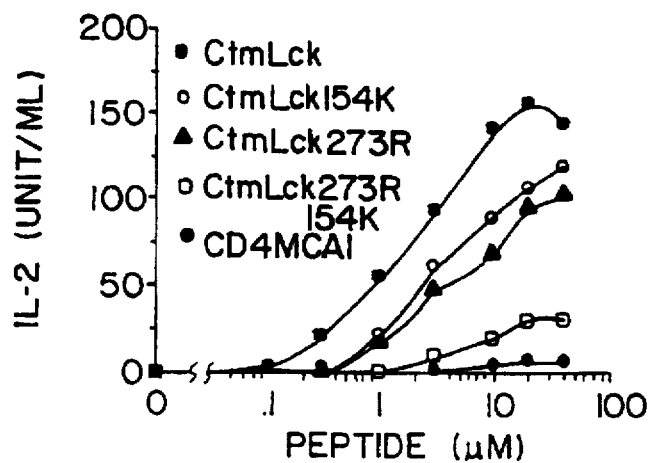
FIGS. 7A–7C illustrate the effect of the SH2 domain on the function of chimeric proteins of the present invention.
Figure 7A:
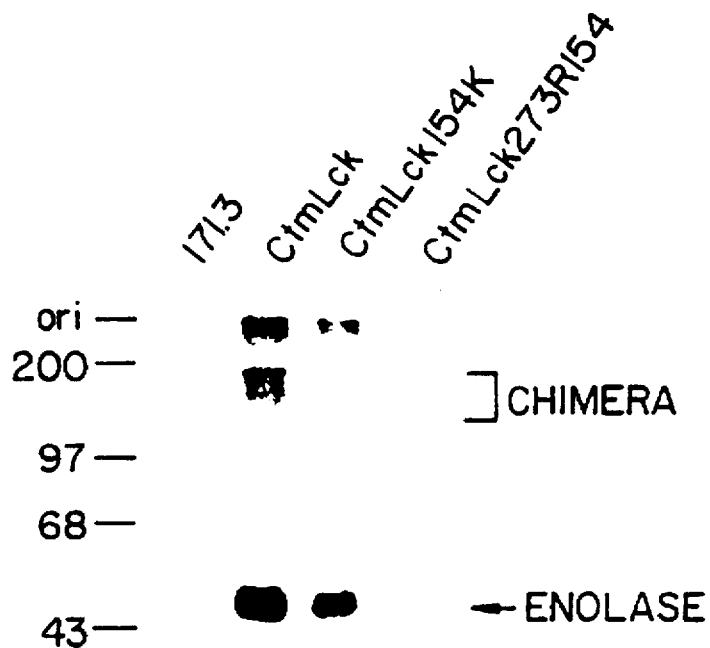
Figure 7B:
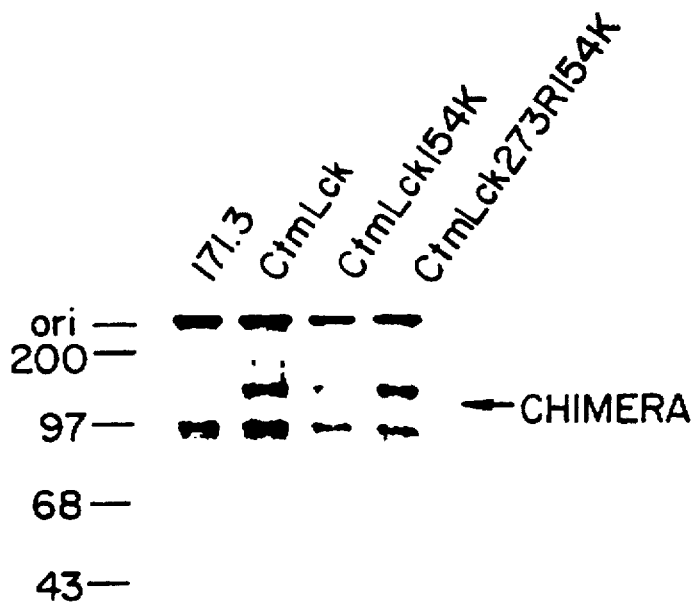

The role of the Lck SH2 domain, which is predicted to bind to specific tyrosine-phosphorylated cellular proteins was analyzed. A point mutation (arg>lys) was introduced at the highly conserved arg154 residue, which is predicted to be located in the phosphotyrosine-binding cleft based on the crystal structure of the homologous v-src SH2 domain (Waksman et al., *Nature*, 358:646–653 (1992), incorporated herein by reference). A similar change in the abl SH2 domain has been shown to abrogate its binding to tyrosine-phosphorylated proteins (Mayer at al, *Mol. Cell. Biol.*, 12:609–618 (1992), incorporated herein by reference. Although this mutation did not affect the ability of the chimera to phosphorylate substrates in vitro (FIGS. 7A & 7B), the mutant protein showed decreased co-receptor activity (CtmLck154K construct in FIG. 7). Significantly, when this SH2 domain mutation was combined with the point mutation (arg-273) that abolished kinase activity, the resulting defect was much more severe than that observed with either mutation alone (FIG. 7C, compare the CtmLck273R154K double mutant with the CtmLck154K and CtmLck273R mutants). The phenotype of the double mutant indicates that Lck works through multiple activities contributed independently by its various domains.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of determining whether a drug is capable of blocking T lymphocyte activation comprising:

contacting the drug with a T lymphocyte that has been transfected with a nucleic acid sequence that encodes a CD4 molecule lacking the CD4 cytoplasmic domain linked to an src protein tyrosine kinase;

the said T lymphocyte expresses a chimeric protein comprising a CD4 molecule lacking the CD4 cytoplasmic domain linked to an src protein tyrosine kinase;

stimulating the said T lymphocyte;

observing the degree of stimulation of the said T lymphocyte; and determining whether the drug is capable of blocking said T lymphocyte activation therefrom.

2. A method as in claim 1, wherein the src protein tyrosine kinase is $p56^{lck}$, c-SRC, Fyn-T, ZAP-70, or Hck.

3. A method as in claim 1, wherein the degree of stimulation of the T lymphocyte is measured by the production of interleukin-2 by the T lymphocyte.

4. A method as in claim 1, wherein said T lymphocyte has been further transfected with a DNA molecule comprising an interleukin-2 promoter operably linked to a nucleic acid sequence encoding reporter proteins and wherein the degree of stimulation of the T lymphocyte is measured by the production of reporter proteins whose expression is controlled by the interleukin-2 promoter.

5. A method as in claim 1, wherein the degree of stimulation of the T lymphocyte is measured by the degree of tyrosine phosphorylation of proteins within the T lymphocyte.

6. A method as in claim 1, wherein the T lymphocyte is stimulated by exposure to an antigen.

7. A method as in claim 1, wherein the T lymphocyte is stimulated by antibody cross-linking.

8. A method for determining whether an antigen of a patient elicits an immune response in the patient, comprising:

transfecting T lymphocytes of the patient with a DNA molecule comprising a nucleic acid sequence encoding a chimeric protein comprising a CD4 molecule lacking the CD4 cytoplasmic domain linked to an src protein tyrosine kinase;

contacting the transfected T lymphocytes with the patient's antigen;

observing stimulation of the T lymphocytes by the antigen; and determining therefrom whether the antigen elicits an immune response in the patient.

9. A method as in claim 8, wherein the T lymphocyte is transfected with the DNA molecule by means of a retroviral vector.

10. A method as in claim 8, wherein stimulation of the T lymphocytes is measured by the degree of production of interleukin-2 by the T lymphocyte or by the degree of tyrosine phosphorylation of proteins within the T lymphocyte.

* * * * *

UNITED STATES PATENT AND TRADEMARK OFFICE
CERTIFICATE OF CORRECTION

PATENT NO. : 5,670,324
DATED : September 23, 1997
INVENTOR(S) : LITTMAN et al.

It is certified that error appears in the above-identified patent and that said Letters Patent is hereby corrected as shown below:

In column 1 at line 7, insert the following statement:
--This invention was made with Government support under Grant No. AI23513, awarded by the National Institutes of Health. The Government has certain rights in this invention.--

Signed and Sealed this

Twenty-second Day of June, 1999

Attest:

Attesting Officer

Q. TODD DICKINSON

Acting Commissioner of Patents and Trademarks